United States Patent [19]
Whitmore

[11] Patent Number: 5,330,479
[45] Date of Patent: Jul. 19, 1994

[54] RECIPROCATING BONE PUNCH

[76] Inventor: Henry B. Whitmore, Rte. 5, Box 369, San Antonio, Tex. 78221

[21] Appl. No.: 29,529

[22] Filed: Mar. 11, 1993

[51] Int. Cl.$^5$ .............................................. A61B 17/00
[52] U.S. Cl. .................................................... 606/79
[58] Field of Search ............... 606/79, 80, 81, 82, 606/86, 87, 88, 176, 178

[56] References Cited

U.S. PATENT DOCUMENTS

| | | | |
|---|---|---|---|
| 2,070,281 | 7/1935 | Leggiadro | 606/82 |
| 4,941,466 | 7/1990 | Romano | 606/80 |
| 5,002,546 | 3/1991 | Romano | 606/80 |

Primary Examiner—Stephen C. Pellegrino
Assistant Examiner—Sonya C. Harris
Attorney, Agent, or Firm—Paul H. Gallagher

[57] ABSTRACT

A casing having an arcuate tool bit at its front end. The tool bit oscillates, having opposite points entering into the bone alternately. The tool bit is driven by a rocking lever, and the lever is driven by a hammer driven by a motor with a flywheel. The arrangement provides a percussion thrust against the lever by the hammer in each of opposite directions.

9 Claims, 2 Drawing Sheets

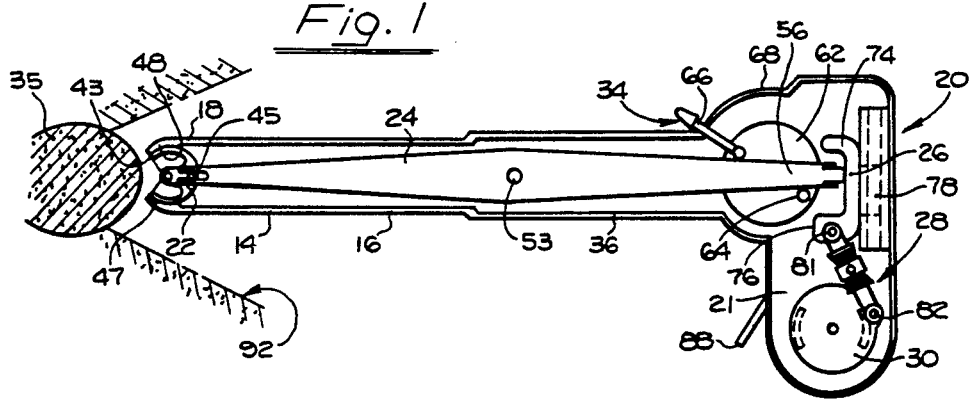
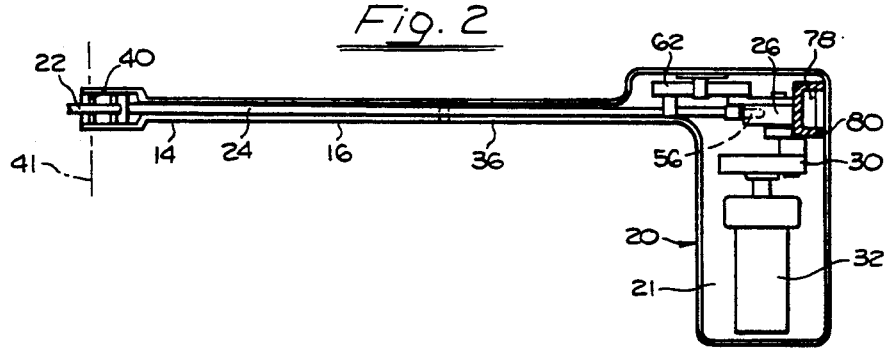
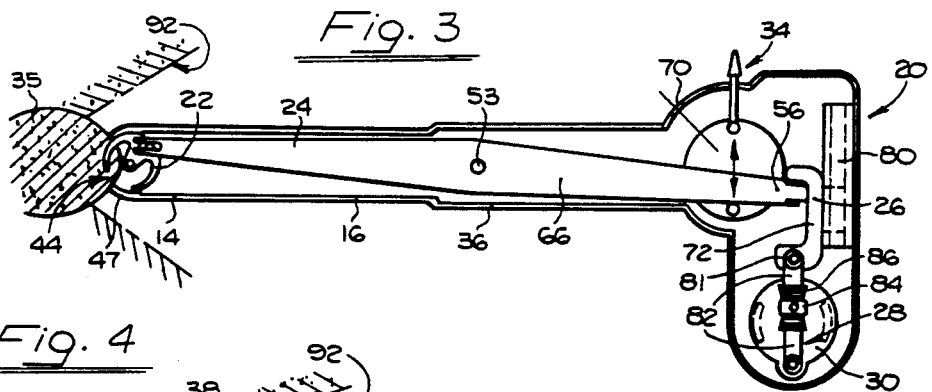
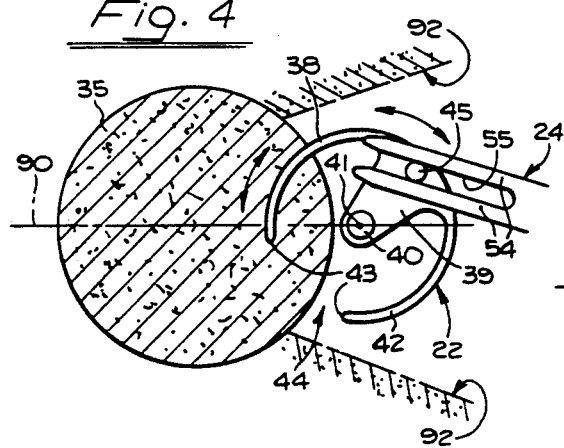
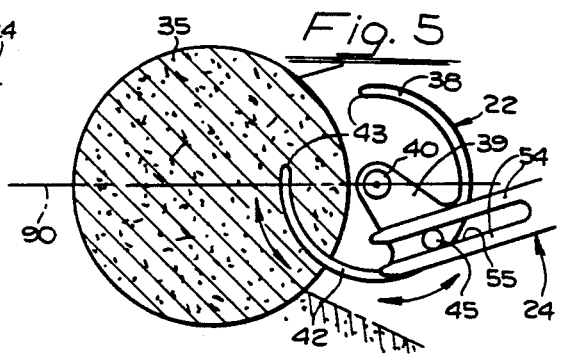

RECIPROCATING BONE PUNCH

BRIEF SUMMARY OF THE INVENTION

The invention resides in the broad field of chiseling or cutting a hole, or tunnel in a bone, in the body, in a surgical operation. An example of the purpose of cutting such a hole is to insert sutures therein for connecting tissues or tendon to the bone.

Heretofore such holes or tunnels were cut in the bone by manual manipulation, such as by using a hammer and chisel. This kind of operation necessitated movements such as swinging movements of the hammer, and holding the chisel by the other hand. The resulting broad or sweeping movements of the hammer were sometimes clumsy and since the holes to be cut were arcuate, or circular in shape, it was extremely difficult to cut them and the manipulation often resulted in inaccurate cutting and damage to bone.

There appears to be no instrument heretofore existing, that would cut such holes in the bone.

A broad object of the invention therefore is to provide an instrument, that is power driven, and of such simple construction and operation, that the user, to perform the desired cutting step, need only apply the instrument to the location on the bone desired, and set the instrument into operation, while holding it stationary in the proper position until the cutting step is completed.

Another feature of the invention has to do with the fact that cutting a hole in a bone necessarily involved impact, or percussion. The absence of any mechanical instrument that would cut the desired hole in a bone, may be because impact or percussion is necessary, and therefore an important feature of the present invention is to provide a mechanical instrument that involves a novel manner of performing impact or percussion steps, automatically in response to turning on the instrument, that cuts the desired hole in the bone.

Other features of the invention are that the instrument is very simple in design and requires only the simplest components, and fabricating steps; it is light in weight, and it is of such design that the user can easily pick up and handle the entire instrument as easily as utilizing various other instruments of simple nature.

BRIEF DESCRIPTIONS OF THE SEVERAL VIEWS OF THE DRAWINGS

FIG. 1 is a longitudinal sectional view of the instrument, in association with a bone in which a hole is to be cut.

FIG. 2 is a view from the top of FIG. 1 with the near element of the casing removed, to expose the interior.

FIG. 3 is a view similar to FIG. 1 but with certain elements in alternate positions.

FIG. 4 is a fragmentary view of the tool bit in association with a bone.

FIG. 5 is a view similar to FIG. 4 but showing the tool bit in a different position.

DETAILED DESCRIPTION

Figure 6:
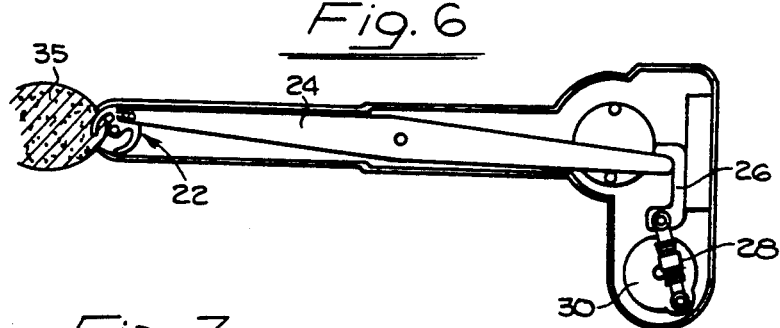
FIG. 6 is a view similar to FIG. 1 but showing the internal operating parts in different positions, in another step of the operation.
Figure 7:
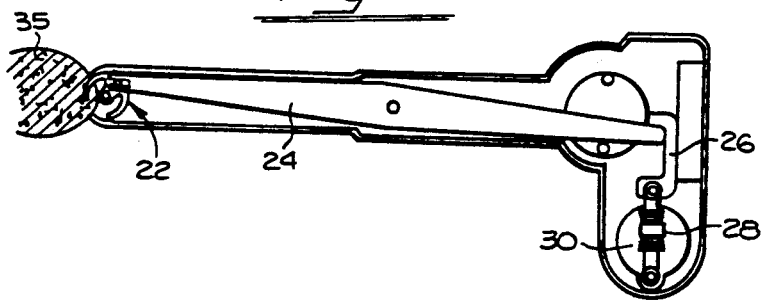
FIG. 7 is a view similar to FIG. 6 but showing the internal parts in different positions.
Figure 8:
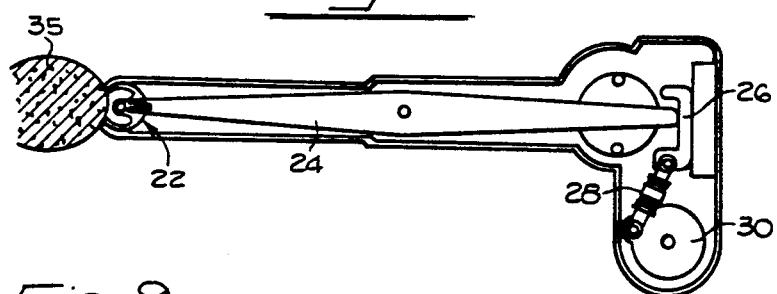
FIG. 8 is a view similar to FIGS. 6 and 7 but showing the internal parts in other positions.

Referring in detail to the drawings, attention is directed first to FIGS. 1-3. The instrument indicated in its entirety at 14 includes a casing 16 having an open front end 18 and a rear end 20, and a chamber 21 at the rear end extending to one side.

Within the casing are the internal operating parts or components, a tool bit 22, which may also be referred to as a chisel or cutter, a lever or rocker arm 24, a hammer 26, a connecting rod 28, a flywheel 30, and a drive motor 32. There is also a centering mechanism 34 which is not used during a surgical operating step. Drive is transmitted from the drive motor to the tool bit, and interpreted downstream in that direction.

For convenience, the surgical instrument will be described as oriented in FIGS. 1-3, and the various locations and directions are to be interpreted according to that position of the instrument. The various components may be made of desired materials, according to known procedures, such as making at least certain of them of stainless steel. The casing 16 may be generally of openwork, or easily disassembled for cleaning purposes. The casing has a main front portion 36 that includes the front end 18. The tool bit 22 is generally flat (FIG. 2) and it is circular in shape, (FIGS. 4 and 5), in the form of a ring 38 including a body portion 39 having a hub, and a shaft or axle 40, an axis 41 extending through the axle. The ring includes circular fingers 42 having opposed cutting points or tips 43 spaced apart, leaving a gap 44. These points actually perform the step of penetrating the bone. An axial pin 45 is provided on the ring, opposite the gap 44.

The tool bit 22 oscillates about the axis 41 which extends transverse to the casing. The open end 18 of the casing terminates forwardly in fingers having tips 47, and the inner surfaces of the fingers are arcuate as at 48 corresponding to the curvature of the tool bit. The open end need not be directed straight longitudinally. The tool bit in a normal or home position is centered as shown in FIG. 1, where the points 43 are adjacent the forward ends of the finger tips 47, but preferably slightly inwardly therefrom. This relationship will be referred to again hereinbelow in the description of the action of the instrument in cutting the hole in the bone.

The lever 36 has a transverse pin 53 at about its middle, by which the lever is mounted in the casing for rocking movements. The lever at its forward end has fingers 54 defining a space 55 therebetween, slidingly receiving the pin 45, in a yoke connection, and the lever has a rear or inner end identified 56. Upon rocking of the lever, the tool bit is oscillated as described hereinbelow.

The centering mechanism 34 is utilized for putting and holding the lever 24, and the tool bit 22, in centered position shown in FIG. 1. This centering mechanism includes a plate or wheel 62 pivoted in the casing on a transverse axis, and it includes diametrically opposite, axially extending pins 64 at its periphery. The wheel is provided with a handle 66 extending through a slot 68 in the casing to the exterior. The handle and the surface of the slot are provided with suitable releasable detent means 70 for releasibly holding the wheel and lever in each of opposite positions, these being an active or centering position shown in FIG. 1 and the opposite or released position shown in FIG. 3. The pins 64 are arranged to engage the lever at the inner end of the latter and when the wheel is in its holding position, the pins engage the lever and hold it in its center position (FIG. 1) and when it is moved to released position (FIG. 3) the lever is free to rock or move up and down.

The hammer 26 is C shaped, having a central body element 72, an upper hook 74 and a lower hook 76, the hooks hammering against the top and bottom of the rear end 56 of the lever, as described below.

The hammer 26 is provided with a slide 78, which may be T-shaped, which rides in a channel in a guide member 80 mounted on the casing, for controlling the vertical movements of the hammer.

The connecting rod 28 is pivoted at points 81, 82 on the hammer and flywheel 30 respectively. This connecting rod includes longitudinally aligned sections that are slidable relative to each other longitudinally, and a collar 84 surrounding the sections. A coil spring 86 surrounds the connecting rod sections, and is connected with both of the sections. The connecting rod is extensible and contractible, as referred to again hereinbelow, and the coil spring acts as a compression/pusher spring, and also as a tension/puller spring, in the contracting and extending movements of the connecting rod. This feature is involved in the percussion action in the cutting or chiseling step, which is an important feature of the invention.

The flywheel 30 is mounted on the drive shaft of the motor and runs continuously, this feature also being tied in with the percussion feature just referred to, as will be referred to again below.

The motor 32 may be an electric motor, as herein, but the drive means may be of any of other sorts, including pneumatic and hydraulic devices. A control hand switch 88 may be provided at any convenient location in the casing.

Attention is directed here to an important feature of the invention—the overall design of the instrument is such that it is easily picked up and handled, in one hand. It may be of any convenient size, such as in the neighborhood of 12 inches long, and it is of very light weight, rendering it easily manipulated. The chamber 20 extends transversely from the elongated portion 26 which adds to the convenience in holding it by the hand, i.e., relative to the exact and accurate positioning of the tool bit when applied to the bone. This chamber may be positioned on the other side instead, for example, if found convenient for a left handed user. As referred to above, cutting into a hard bone necessitates the use of percussion. The provision of the percussion is extremely important, and it is emphasized at this point that the percussion is achieved by the relationship between the hammer 26 and the inner end of the lever 24. There is not constant interengagment between those two members.

Attention is directed to FIGS. 6–10 which show the steps of the movement of the hammer and the lever in a complete cycle, which takes place in one complete revolution of the flywheel 30 to which the connecting rod is connected. These figures can be considered in connection with FIG. 1 which shows the lever 24 in centered position, and the tool bit 22 correspondingly in centered position, with both of the cutting points of the tool bit retracted and within the casing. The instrument is applied to the bone by engaging the points 47 directly against the bone, whereby the instrument can be held steady and in accurate position.

In using the instrument, and after moving the centering means 62 to released position of FIG. 3, the drive motor 32 is operated. In the centered position of FIG. 1, the hammer assumes approximately a centered position, neither end engaging the lever. Upon operating the drive motor, the flywheel is rotated, clockwise, and the connecting rod moves down to the position shown in FIG. 6, or nearly its lowermost position. The hammer, in going from the position of FIG. 1 to that of FIG. 6 abruptly engages the lever, causing the percussion step. In the position of FIG. 6, the inner end of the lever is in its lowermost position, and the hammer cannot proceed further, but upon continued movement of the flywheel, and the connecting rod, from the position of FIG. 6 to that of FIG. 7, the hammer does not move further, and the connecting rod is necessarily extended. This extension feature was referred to above. Then in the continued movement of the flywheel and connecting rod from the position of FIG. 7 to that of FIG. 8, the lower end of the connecting rod moves to a position approximately half way to the top, and at this step the connecting rod contracts in length, and the hammer is driven upwardly to approximately its center position.

Figure 9:
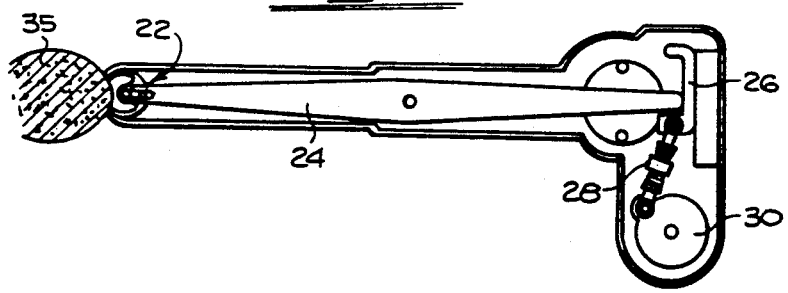
FIG. 9 is a view similar to FIGS. 6-8 but showing the internal parts in still different positions.
Figure 10:
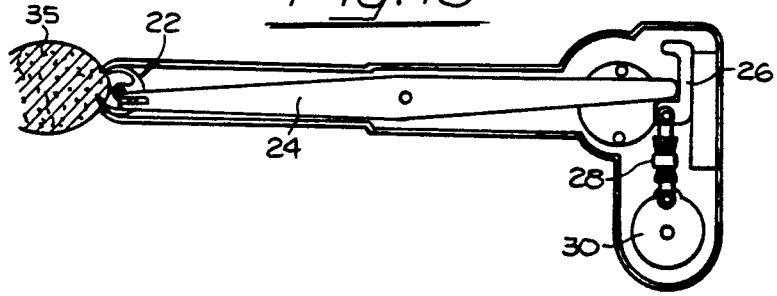
FIG. 10 is a view similar to FIGS. 6-9 but showing the internal elements in yet different positions.

Upon continued movement of the connecting rod, the hammer again strikes the inner end of the lever in a percussion step, in the position of FIG. 9, wherein the lower hook of the hammer is in engagement with the lever. The connecting rod is not yet at its uppermost position, and upon continued upward movement from the position shown in FIG. 9, the hammer moves the inner end of the lever upwardly. After the position of FIG. 10, the continued movement of the flywheel moves the hammer to the position of FIG. 1, which was the starting position of this cycle.

Thus in each cycle, one revolution of the flywheel, there are two percussion steps performed, one on the movement of the hammer downwardly, and the other on its movement upwardly. The flywheel thus functions as a means for oscillating the lever 24.

As referred to above, this movement of the lever is transmitted to the tool bit 22, causing corresponding percussion movements of the tool bit. Reference is made to FIGS. 1, 4 and 5 for details of the specific action of the tool bit. In the use of the device, the open front end of the casing is placed against the bone, as stated, with the tool bit in centered position, and the drive motor is turned on, and the tool bit reciprocated. In the reciprocation of the tool bit, it moves in one direction, e.g., counterclockwise (FIG. 4) and the point 43 on that side strikes the bone and chips away at it. Then upon rocking movement of the lever in the opposite direction, the tool bit is oscillated in clockwise direction, retracting the upper point from the bone, and of course forcing the lower point against the bone, and in the case of both points, increasingly chipping away at the bone until the points actually are forced through the outer hard surface and into the interior.

In FIGS. 4 and 5 is a reference line 90 intersecting the axis of the tool bit, and extending through the bone at approximately the center of the bone. The various dimensions and proportions of the operating parts are so preselected that in the oscillating movements of the tool bit, the points of the fingers ultimately penetrate at least to the center line 90, and preferably they go slightly therebeyond. This degree of penetration assures that the two points together in their respective penetrating movements, form a continuous hole through the bone. It is important that neither of the points moves to the opposite end of the hole and penetrates through the outer hard surface from the inside. Thus the end edges of the hole, through the hard outer layer of the bone, at both ends, are formed accurately and without jagged edges. In penetrating through the hard layer, the chips of course will fall, but as the cutter points enter into the inner soft portion of the bone, they merely push it or compact it to the side, and form a smooth round hole.

The extent of the angular movements of the tool bit 22 and the lever 24 are predetermined to produce the linear extent of movements desired, and to limit further movement, and to hold the elements in their desired position. The lever 24 moves through an angle of in the neighborhood of 5°, engaging surfaces of the casing, which limits its throw in the respective directions. The tool bit oscillates through an angle in the neighborhood of 80° and this is of course determined by its own size or diameter in association with the throw of the lever. It will be noted that the pin 45 slides in the slot 56, forming the yoke connection referred to and this of course accommodates the movement of the pin longitudinally of the slot.

The importance of this specific manner of forming the hole in the bone is emphasized. The bone is formed clean-cut, and the wide range swinging of a hammer with a chisel is eliminated. Additionally the opening or hole in the flesh to reach the bone is at a very minimum. This opening is shown at 92 in FIG. 3, and it need be only slightly greater than the vertical dimension of the front part 36 of the casing.

Another very important feature of the invention is emphasized. The flywheel 30 provides steady movement of the lower end of the connecting rod and that movement together with the provision of the coil spring 86 provides the percussion or impact desired. As referred to above, at each end of the throw of the hammer, the corresponding end reaches a position spaced from the inner end of the lever, and upon reverse movement of the hammer, it abruptly engages the lever, producing that percussion.

I claim:

1. A surgery bone chisel instrument comprising,
 a casing having an open front end,
 a tool bit having cutting elements lying in a circle with tips spaced apart and directed toward each other, and having an actuating element diametrically opposite the tips,
 the tool bit including a shaft mounted in the casing adjacent the open front end of the casing with its axis disposed transverse to the casing, and oscillatable on that axis, and operable in response to such oscillation for alternately extending the tips through the open front end of the casing, and
 means for oscillating the tool bit, including a driver in the casing at a rear end of the casing, a lever in the casing rockable on a transverse axis at a midpoint of the lever,
 the lever at the front end having operable connection with said actuating element, and at its rear end with the driver, 2. An instrument according to claim 1 and including,
 a hammer corresponding to the rocking movements of the rear end of the lever and engageable therewith in each of opposite directions, with play therebetween in each direction,
 an extensible/contractible connecting rod,
 oscillating means,
 the connecting rod being connected at one end to the hammer, and at its other end to the flywheel, and
 power means for driving the oscillating means and thereby the hammer.

3. A instrument according to claim 2 wherein,
 the connecting rod includes longitudinally positioned and slidable rigid parts, and
 a tension/compression spring interconnecting the parts.

4. An instrument according to claim 2 wherein,
 the instrument has an upright operable position, thereby defining a vertical direction,
 the casing including a front portion of relatively greater vertical dimension relative to a thin transverse dimension,
 the tool bit and lever being of plate-like shape complementary to the cross sectional dimensions of said front portion of the casing,
 the casing including a chamber rearwardly of said front portion, and the hammer, connecting rod, flywheel, and power means being contained in said chamber.

5. An instrument according to claim 2 wherein,
 the oscillating means is a flywheel.

6. An instrument according to claim 1 wherein,
 the casing has an elongated front portion, and a chamber at the rear end extending generally transverse to the front position, and having a control means adjacent the chamber for controlling the driver,
 the casing containing and effectively enclosing all the elements except for an exposed portion of the switch, and
 thereby the instrument as exemplified by the casing can be bodily and entirely held in the hand for use in operating on a bone.

7. An instrument according to claim 1 wherein,
 the means for oscillating the tool bit includes releasable means for holding the lever and thus the tool bit stationary throughout a dwell period, and
 means operable on release of the holding means for imposing an abrupt percussion movement on the lever and thus on the tool bit to oscillate the tool bit.

8. An instrument according to claim 7 wherein,
 a drive transmitting means includes adjacent operable drive elements, having spacing therebetween, and those drive elements upon interengagement thereby producing percussion to the movement of the tool bit.

9. An instrument according to claim 8 wherein,
 the drive transmitting means includes an extensible and contractible connecting rod operable for moving said drive elements into driving interengagement.

* * * * *